United States Patent [19]

Harvey et al.

[11] Patent Number: 5,447,940
[45] Date of Patent: Sep. 5, 1995

[54] ABSORBABLE COMPOSITE MATERIALS FOR USE IN THE TREATMENT OF PERIODONTAL DISEASE

[75] Inventors: Wilson Harvey, Sterling; Nicholas D. Light, Doune Perthshire; Carla A. Haynes, Glasgow, all of United Kingdom

[73] Assignee: Johnson & Johnson Medical, Inc., Arlington, Tex.

[21] Appl. No.: 280,917

[22] Filed: Jul. 27, 1994

[30] Foreign Application Priority Data

Jul. 28, 1993 [GB] United Kingdom ............. 9315614

[51] Int. Cl.⁶ ................. A01N 43/42; A61K 31/47
[52] U.S. Cl. ................. 514/310; 424/435; 424/443; 424/444
[58] Field of Search ........... 514/310; 424/435, 443, 424/444

[56] References Cited

U.S. PATENT DOCUMENTS

| | | | |
|---|---|---|---|
| 4,175,326 | 11/1979 | Goodson | 424/19 |
| 4,251,507 | 2/1981 | Olson | 424/49 |
| 4,304,765 | 12/1981 | Shell et al. | 424/22 |
| 4,568,535 | 2/1986 | Loesche | 424/19 |
| 4,685,883 | 8/1987 | Jernberg | 433/215 |
| 4,764,377 | 8/1988 | Goodson | 424/435 |
| 4,789,662 | 12/1988 | Thomas-Leurquin et al. | 514/21 |
| 4,849,141 | 7/1989 | Fujioka et al. | 264/207 |
| 4,892,736 | 1/1990 | Goodson | 424/435 |
| 4,906,670 | 3/1990 | Higashi et al. | 514/773 |
| 4,933,182 | 6/1990 | Higashi et al. | 424/435 |
| 4,961,707 | 10/1990 | Magnusson et al. | 433/215 |
| 5,002,769 | 3/1991 | Friedman | 424/422 |
| 5,198,220 | 3/1993 | Damani | 424/426 |

FOREIGN PATENT DOCUMENTS

| | | |
|---|---|---|
| 194192 | 9/1986 | European Pat. Off. . |
| 297535 | 1/1989 | European Pat. Off. . |
| 388220 | 9/1990 | European Pat. Off. . |
| WO92/10218 | 6/1992 | European Pat. Off. . |
| 567234 | 10/1993 | European Pat. Off. . |
| 0140766 | 5/1985 | United Kingdom . |
| 0250187 | 12/1987 | United Kingdom . |

OTHER PUBLICATIONS

European Patent Standard Search Report for EP 94305537 dated Nov. 11, 1994.

*Primary Examiner*—Arthur C. Prescott

[57] ABSTRACT

Absorbable composite materials are described that comprise a collagen matrix reinforced with a layer of a bioabsorbable polymer. A chemotherapeutic agent is dispersed in the composite material. The layer of bioabsorbable polymer is preferably a woven, nonwoven or knitted mesh layer of a synthetic bioabsorbable polymer such as polylactic/polyglycolic acid copolymer, or oxidised regenerated cellulose. The chemotherapeutic agent may be an antibiotic, an anaesthetic, an antiseptic or an anti-inflammatory. Strips of the composite material are inserted into the periodontal pocket, where they are retained in place and provide effective sustained release of the chemotherapeutic agent over an extended period.

15 Claims, No Drawings

ABSORBABLE COMPOSITE MATERIALS FOR USE IN THE TREATMENT OF PERIODONTAL DISEASE

The present invention relates to absorbable composite materials in the form of a strip or film that are specially adapted for the treatment of periodontal disease.

"Periodontal disease" is the term commonly used to describe inflammatory disease of the periodontium (tooth-surrounding tissue). It is a widespread disease in mammals, particularly humans, and chronic inflammatory periodontal disease (CIPD) is the major cause of tooth loss in adults.

CIPD results from the accumulation of dental plaque in the gingival crevice, i.e. the gap between the gingiva and the tooth, which is normally about 1 mm deep. The epithelial attachment to the tooth forms a barrier between the external environment in the mouth and the tooth-supporting tissues. An increase in dental plaque leads to gingivitis, and successive inflammatory reactions cause the progressive erosion of the tooth-supporting tissues which are the collagenous fibres and the bone socket in which the tooth sits. This erosion is manifested by an enlargement of the gingival crevice which may become many millimeters deep.

Treatment of CIPD has traditionally been focused on the destruction or removal of the bacterial plaque whose accumulation perpetuates the disease. This is commonly practised by one or both of two approaches: surgical intervention and non-surgical treatment. The surgical approach comprises reflecting the gingival tissues to expose the tooth root in order that mechanical removal of the plaque may be accomplished directly, by e.g. scraping, the use of ultrasonics or laser methods. Following this debridement, the gingival tissue is sutured back in position. This procedure is time-consuming, painful and requires substantial specialist resources.

The non-surgical approach usually comprises limited mechanical debridement (e.g. scraping and irrigation) via the entrance to the periodontal pocket, followed by antibacterial chemotherapy. This chemotherapy may take the form of systemic antibiotics, of which tetracyclines and imidazoles are commonly used, or the localised application of the antibacterial agent via the periodontal pocket. In addition to antibiotics, antiseptics such as chlorhexidine can be introduced to the periodontal tissues in this manner. Advantages of the local administration of antibacterial agents are the relatively higher concentrations achievable in the periodontal tissues, compared with those obtained by systemic therapy, and also a decreased risk of producing bacterial resistance to the agent. Furthermore, the use of the non-surgical approach is less traumatic for the patient and is less demanding on professional resources.

For these reasons, the treatment of CIPD by non-surgical intervention and locally-applied antimicrobial agents is gaining popularity. However, there is a major problem with the delivery of the antimicrobial agent to the tissues, and more particularly with maintaining sufficiently high concentrations to be therapeutically efficaceous in a manner which is practical and acceptable to the patient. The introduction of the agent into the periodontal pocket by the injection of a solution (e.g. by syringe or pulsed-jet irrigation, see Newman, J. Clin Periodontal, 1986, 13: 965–974) often results in rapid loss of the agent from the site, either by exudation into the oral cavity or by rapid diffusion and dilution in the surrounding tissues, thereby requiring repeated applications which are impractical. This has led to the need for an appropriate system or 'vehicle' for the sustained delivery of the therapeutic agent in order to maintain pharmacologically-effective concentrations for an acceptably long period following a single administration. Considerable efforts have been made by many in the field to devise such a carrier with the requisite degree of bioacceptibility, mechanical characteristics, retention time and controlled release properties.

For example, U.S. Pat. No. 4,685,883 (Jernberg) describes a method of local delivery of chemotherapeutic agents to the periodontal pocket by inserting into the periodontal pocket time-release microspheres comprising the chemotherapeutic agent dispersed in a biodegradable solid. A drawback of this method is that the time-release microspheres tend to leak out of the periodontal pocket.

U.S. Pat. No. 4,892,736 (Goodson) describes a system for delivering a chemotherapeutic agent to the site of a periodontal infection which comprises a biodegradable fibre such as an ethylene vinyl acetate (EVA) copolymer fibre containing the chemotherapeutic agent. A length of the fibre is inserted into the periodontal pocket, and is retained there by a retaining means such as an elastic band. A drawback of this system is that the retaining means tends to cause irritation of the infected gum tissue.

U.S. Pat. No. 4,933,182 (Higashi et al.) describes a controlled-release pharmaceutical composition in the form of a gel, sheet, film or bar to be inserted into a periodontal pocket. The composition comprises a chemotherapeutic agent dispersed in a two-phase carrier consisting of: (a) a continuous phase of a water-soluble polymer, and (b) a discontinuous phase of solid particles that are soluble in the pH range 4.0 to 6.0.

U.S. Pat. No. 4,789,662 (Thomas-Lerquin et al.) describes a method of treating periodontal disease by inserting into the periodontal pocket a collagen film having a chemotherapeutic agent dispersed therein. The collagen film biodegrades slowly in the periodontal pocket to release the chemotherapeutic agent.

U.S. Pat. No. 4,906,670 (Higashi et al.) describes a medicated film for insertion into the periodontal pocket to provide sustained release of a chemotherapeutic agent. The film consists of the chemotherapeutic agent dispersed in glutaraldehyde cross-linked succinylated atelocollagen gel in a 1 to 9 ratio with hydroxypropylcellulose.

EP-A-0388220 (Yissum) describes periodontal implants consisting of an effective amount of chlorhexidine gluconate in a water insoluble protein matrix. The protein preferably comprises cross-linked gelatin, albumin, an enzyme or fibrinogen. The implant may also contain a plasticiser such as glycerol.

The above-described medicated films for the treatment of periodontal disease provide the advantages of ease of insertion into the periodontal pocket, followed by slow release of a chemotherapeutic agent over a period of time. The films themselves may be formed of biodegradable materials that are compatible with the periodontal pocket and do not interfere with healing.

However, up until now no completely satisfactory slow-release film for the treatment of periodontal disease has been developed. This is because of the following conflicting requirements for the properties of the film.

The first requirement is that the film should be stiff when dry so that it is easy for the dental practitioner to handle and easy to insert deep into the periodontal pocket.

The second requirement is that the film should be soft and conformable in use, i.e. after it has been inserted into the periodontal pocket. This is to avoid irritation of the periodontal pocket by the inserted film.

The third requirement is that the film should be retained in the periodontal pocket for extended periods without falling out either spontaneously or as a result of normal oral hygiene measures, such as flossing or brushing, which are required to maintain gingival health.

The fourth requirement is that the film should release the chemotherapeutic agent at a slow, controllable rate over an extended period. Preferably, the film should remain effective for up to 30 days in situ, since inserting a replacement film is inevitably somewhat traumatic to the periodontal pocket.

EP-A-0194192 (Ethnor) describes a bioabsorbable composite material for use as a graft or prosthesis in surgery. The material comprises a woven or knitted mesh of resorbable fibres (such as fibres of a copolymer of lactic acid and glycolic acid) embedded in a continuous film of collagen. The collagen film renders the composite watertight, e.g. for use as an arterial graft. The underlying fibrous structure provides sufficient mechanical strength for the composite to hold sutures. However, there is no suggestion that these composites could be used for controlled release of chemotherapeutic agents.

It has now been found that slow-release chemotherapeutic films that are outstandingly suitable for the treatment of periodontal disease may be made by dispersing chemotherapeutic agents in composite materials similar to those disclosed in EP-A-0194192.

Accordingly, the present invention provides a composite material for use in the treatment of periodontal disease, the composite material comprising a collagen matrix reinforced with a layer of a bioabsorbable polymer and having a chemotherapeutic agent dispersed therein.

Preferably, the collagen is reinforced by a layer of a synthetic bioabsorbable material or a modified cellulose or an alginate. The layer may be in the form of a continuous or perforated sheet or web. Preferably, the layer is a mesh of woven, nonwoven or knitted fibres. Preferred bioabsorbable polymers include suture materials such as copolymers of lactic acid and glycolic acid, or oxidised regenerated cellulose. A particularly preferred synthetic bioabsorbable polymer is the polylactic/polyglycolic acid copolymer sold under the Registered Trade Mark VICRYL. Also particularly preferred is the oxidised regenerated cellulose mesh sold under the Registered Trade Mark SURGICEL.

The collagen matrix may comprise insoluble Type I and/or Type III collagen fibres. Alternatively or additionally the collagen matrix may comprise soluble collagen, such as gelatin or atelocollagen or acid soluble collagen, or even collagen fibres reconstituted from these soluble collagens. The collagen may be obtained from any animal, fish or avian source, but is preferably obtained from bovine corium.

The relative amounts of collagen and bioabsorbable polymer mesh in the composite materials according to the present invention may vary widely, depending on the physical characteristics and the rate of dissolution of the composite material that are required. The composite preferably comprises from 10% to 95% by weight of collagen and more preferably 20% to 60% by weight of collagen.

The chemotherapeutic agent may comprise an antibiotic such as tetracycline, neomycin or metranidazole. Alternatively or additionally the chemotherapeutic agent may comprise a local anaesthetic such as benzocaine or lidocaine. Alternatively or additionally the chemotherapeutic agent may comprise an antiseptic such as iodine, chlorhexidine or a phenolic antiseptic. Alternatively or additionally the chemotherapeutic agent may comprise an anti-inflammatory such as hydrocortisone or indomethacin.

The chemotherapeutic agent is preferably dispersed in the collagen matrix, but it may alternatively or additionally be dispersed in the material of the reinforcing layer. Different chemotherapeutic agents may be dispersed in the collagen matrix and the reinforcing layer so as to achieve phasic release of the different chemotherapeutic agents.

The chemotherapeutic agent is preferably present in an amount of 0.01% to 10% by weight based on the weight of the composite material. More preferably, the chemotherapeutic agent is present in an amount of from 0.1% to 5% by weight based on the weight of the composite material.

The collagen matrix preferably also contains up to 5% by weight, based on the weight of the composite, of an anionic polysaccharide such as an alginate or a glycosaminoglycan, for example hyaluronic acid or chondroitin sulphate. These anionic polysaccharides have soothing and humectant properties and are believed to assist wound healing.

The collagen matrix preferably also contains up to 20% by weight based on the weight of the composite of a plasticiser. Preferred plasticisers include the polyhydric alcohols such as glycerol.

In preferred embodiments the collagen matrix may also contain a dispersed oil phase. That is to say, the collagen matrix may have microdroplets of an oil distributed through it. It has been found that incorporation of such an oil phase into the collagen matrix reduces the rate of absorption of the composite material when implanted in the periodontal pocket, and also reduces the rate of release of the chemotherapeutic agent. As a result, incorporation of the oil phase permits even greater control over the sustained release of the chemotherapeutic agent. Furthermore, the oil phase provides an excellent vehicle for hydrophobic chemotherapeutic agents such as metranidazole.

The oil phase may be a vegetable oil such as corn oil, sesame seed oil or sunflower seed oil, an animal oil such as fish oil, or a mineral oil. The oil is preferably present in an amount of from 1% to 20% by weight, based on the weight of the composite material.

The composite materials according to the present invention are preferably made as follows. First, a slurry of insoluble collagen and/or a solution of soluble collagen in a dilute aqueous acid is prepared. Then other ingredients of the collagen matrix such as the chemotherapeutic agent, the anionic polymer and the plasticiser are added to the slurry and the slurry is homogenised. If the collagen matrix is to contain a dispersed oil phase, then the oil is added to the slurry and homogenised at high shear to emulsify the oil. An emulsifier may optionally be added with the oil, but is usually unnecessary because collagen itself acts as an emulsifier.

The homogenised collagen slurry is then poured over the reinforcing layer, which has been laid out in a flat-bottomed tray. Once the reinforcing layer is covered with the slurry, the water is removed by air-drying or freeze-drying, to leave a sheet of the composite material.

The reinforcing layer is preferably a layer of commercially available VICRYL or SURGICEL mesh fabric.

The composite materials according to the present invention are preferably formed as flat sheets having a preferred thickness of 0.5–2.0 mm. The sheets are cut into strips, typically measuring 1–10 mm by 1–10 mm, and these strips are then inserted into the periodontal pocket.

Some embodiments of the present invention, and their method of manufacture, will now be described further by way of example.

EXAMPLE 1

A composite material comprising an insoluble collagen matrix having chlorhexidine and calcium alginate dispersed therein is prepared as follows:

Fibrous collagen, prewashed to remove the majority of non-collagenous components as described in U.S. Pat. No. 4,614,794 or U.S. Pat. No. 4,320,201 is suspended in clean deionised pyrogen-free water and homogenised to a fine fibrous suspension by passage through a homogenising system, such as described in U.S. Pat. No. 4,320,201. The collagen suspension is then acidified with 0.05M acetic acid to form a swollen fibrous dispersion.

A homogenised suspension of calcium alginate fibres is mixed with a solution of chlorhexidine digluconate in a ratio of 1:1 (w/w) and then blended with the suspension of collagen fibres in 0.05 m acetic acid. The mixture is degassed and poured onto a sheet of Vicryl polylactide/polyglycolide polymer (Registered Trade Mark) and dried under a stream of filtered air at room temperature. The dried composite material is cut into 10 mm×2 mm strips.

EXAMPLE 2

A composite material comprising a soluble collagen matrix having chlorhexidine and calcium alginate dispersed therein is prepared as follows:

Soluble atelopeptide collagen is obtained from limed or unlimed bovine corium by extraction with pepsin. Finely diced, pulped or minced hide is added to 0.05M acetic acid and agitated for 24 hours with pepsin (50:1 collagen:pepsin, w/w) at 20° C. Insoluble residue is removed by centrifugation and the pepsin in the supernatant deactivated by raising the pH to 8.0 with ammonium hydroxide. The solution of atelocollagen is reacidified with acetic acid, precipitated with NaCl (5%, w/v) centrifuged, and redissolved in 0.05M acetic acid.

A homogenised suspension of calcium alginate fibres is mixed with a solution of chlorhexidine gluconate in a ratio of 1:1 (w/v) and then blended with the solution of atelocollagen in 0.05M acetic acid. The mixture is degassed and poured onto a layer of SURGICEL (Registered Trade Mark) oxidised regenerated cellulose mesh and dried under a stream of filtered air at room temperature.

EXAMPLE 3

A composite material comprising a cross-linked collagen matrix having chlorhexidine and calcium alginate dispersed therein is prepared as described in Example 2 above, with the additional step of cross-linking carried out on the collagen-chlorhexidine-alginate solution using carbodiimide prior to degassing and pouring onto a vicryl mesh.

EXAMPLE 4

A composite material wherein the collagen matrix is further reinfored by the addition of fibres of oxidised cellulose is prepared as in Example 1 above, with the additional step of adding finely milled fibres of oxised cellulose (obtained by carding SURGICEL fabric) to the collagen-chlorhexidine slurry prior to degassing and pouring the slurry onto a VICRYL mesh layer.

EXAMPLE 5

A further composite material wherein the collagen matrix is further reinforced by the presence of oxidised regenerated cellulose is prepared by, first, dissolving oxidised cellulose fibres in 0.01M ammonium hydroxide, followed by adding this solution to a solution of atelocollagen in 0.05M acetic acid prepared as in Example 2. The resulting precipitated material is homogenised to form a slurry, chlorhexidine is added to the slurry as described in Examples 1 and 2, and the slurry is then degassed. The degassed slurry is poured onto a sheet of VICRYL mesh and dried under flowing filtered air at room temperature.

EXAMPLE 6

A composite material wherein the collagen matrix comprises a dispersed oil is prepared as follows: 1.68 g of insoluble bovine fibrous collagen is dispersed in 598.5 ml of 0.05M acetic acid solution. 1.8 g of chlorhexidine gluconate is added to the dispersion, followed by 0.18 g of vegetable oil and 0.12 g of glycerol. The mixture is homogenised in a Waring blender. The resulting oil-in-water emulsion is poured over a layer of VICRYL mesh in a PVC tray (320 mm×500 mm) and dried under flowing filtered air at room temperature.

EXAMPLE 7

A composite material wherein the collagen matrix has dispersed therein both an oil phase and metranidazole as the active agent is prepared as follows. 1.62 g of fibrous insoluble bovine collagen is dispersed in 593 ml of 0.05 m acetic acid. 0.18 g of sodium alginate is also dissolved in the acetic acid. 1.5 g of metranidazole is dissolved in 5.0 g of vegetable oil, which is then homogenised with the collagen-acetic acid-alginate slurry in a Waring blender. The resulting emulsion is poured onto a layer of SURGICEL mesh fabric in a PVC tray (320 mm×500 mm) and dried in flowing filtered air at room temperature.

The composites described above have been found to be exceptionally suitable for the treatment of periodontal disease. The composite materials are easy to handle and to cut into any desired shape. Strips of the materials are sufficiently rigid to be inserted deep into the periodontal pocket. Once inserted, the materials absorb fluid within minutes to become soft, conformable and comfortable while maintaining good structural integrity. The absorbed fluid causes the materials to swell so that they fill the periodontal pocket and are held firmly in place by the swelling pressure, without the need for any additional retaining means, for up to 30 days.

This provides for sustained release of the chemotherapeutic agents over an extended period without the need to insert a fresh strip every few days. The composite materials are completely biocompatible and absorbable.

The above examples are intended by way of illustration only. Many alternative embodiments falling within the scope of the accompanying claims will be apparent to the skilled reader.

We claim:

1. A composite material for use in the treatment of periodontal disease, comprising a collagen matrix reinforced with a layer of a bioabsorbable polymer and having a chemotherapeutic agent dispersed therein.

2. A composite material according to claim 1 wherein the collagen matrix comprises insoluble collagen.

3. A composite material according to claim 1 wherein the layer of a bioabsorbable polymer comprises a woven, nonwoven or knitted mesh of the bioabsorbable polymer.

4. A composite material according to claim 1 wherein the bioabsorbable polymer is a synthetic bioabsorbable polymer or a modified cellulose.

5. A composite material according to claim 4 wherein the bioabsorbable polymer comprises a copolymer of lactic acid and glycolic acid or oxidised regenerated cellulose.

6. A composite material according to claim 1 wherein the chemotherapeutic agent comprises an antibiotic, an anaesthetic, an antiseptic or an anti-inflammatory.

7. A composite material according to claim 1 wherein the chemotherapeutic agent is present in an amount of 0.01% to 10% by weight, based on the weight of the composite material.

8. A composite material according to claim 7 wherein the chemotherapeutic agent is present in an amount of from 0.1% to 5% by weight, based on the weight of the composite material.

9. A composite material according to claim 1 wherein the matrix further comprises an anionic bioabsorbable polymer in an amount up to 10% by weight, based on the weight of the composite material.

10. A composite material according to claim 1 wherein the matrix further comprises a plasticiser.

11. A composite material according to claim 10, wherein the plasticiser is a polyhydric alcohol.

12. A composite material according to claim 1 further comprising an oil phase dispersed in the collagen matrix.

13. A composite material according to claim 12 wherein the oil is present in an amount of from 1% to 20% by weight, based on the weight of the composite material.

14. A composite material according to claim 1 in the form of a sheet or strip having a thickness of from 0.5 to 2.0 mm.

15. Use of a composite material according to claim 1 in the preparation of a medicament for the treatment of periodontal disease.

* * * * *